Figure 1:
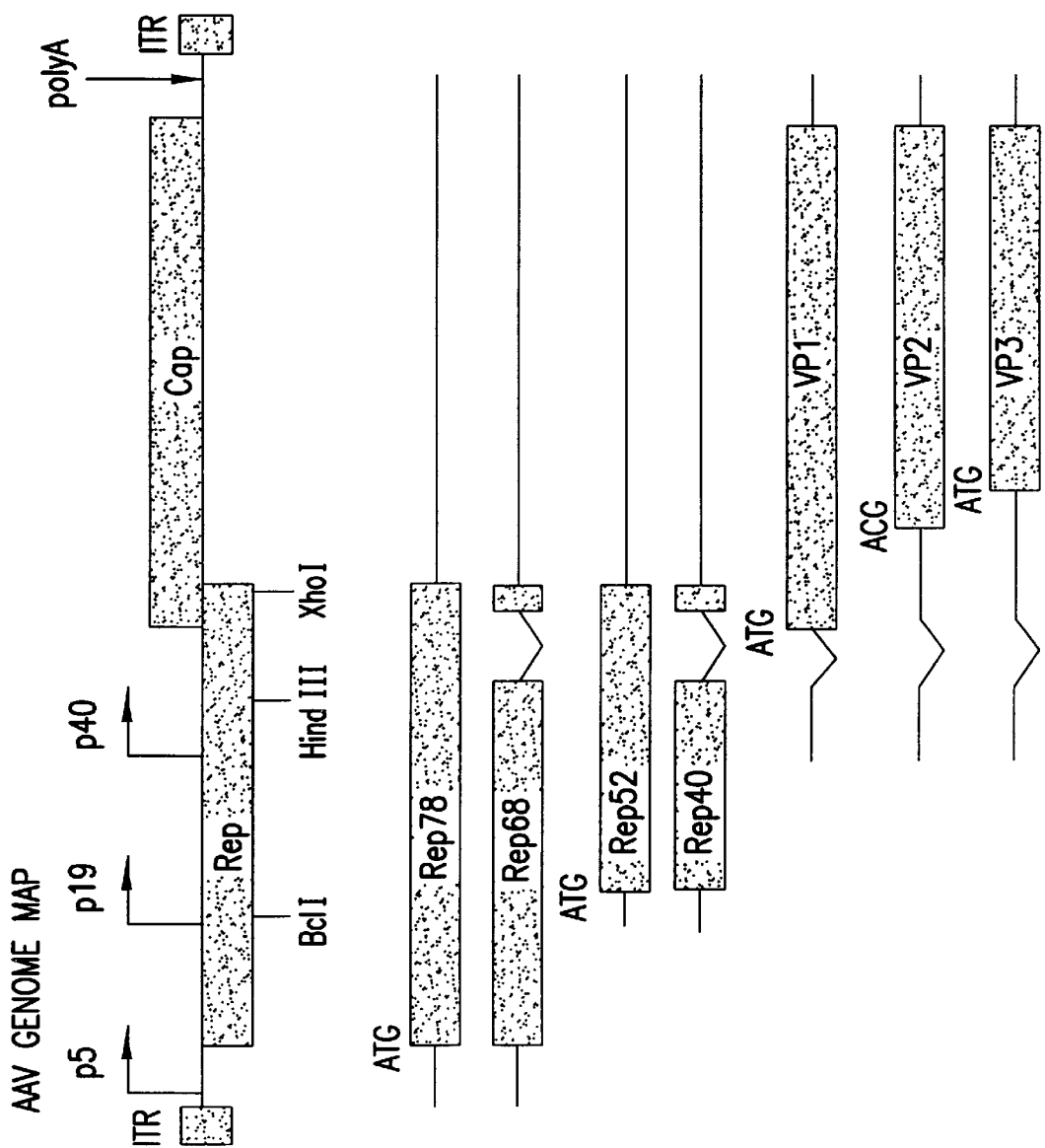

United States Patent [19]
Snyder

[11] Patent Number: 6,037,177
[45] Date of Patent: Mar. 14, 2000

[54] METHOD FOR INCREASING THE EFFICIENCY OF RECOMBINANT AAV PRODUCTION

[75] Inventor: Richard Snyder, Oakland, Calif.

[73] Assignee: Cell Genesys, Inc., Foster City, Calif.

[21] Appl. No.: 08/908,578

[22] Filed: Aug. 8, 1997

[51] Int. Cl.[7] .............................. C12N 5/10; C12N 15/63; C12N 15/35

[52] U.S. Cl. .................... 435/455; 435/354; 435/357; 435/365; 435/366; 435/369; 435/320.1

[58] Field of Search .............................. 435/172.1, 172.3, 435/69.1, 320.1, 325, 366, 367, 369, 455, 354, 357, 365

[56] References Cited

U.S. PATENT DOCUMENTS 5,436,146  7/1995  Shenk et al. ............................ 435/457

OTHER PUBLICATIONS

Koeberl et al., 1997, "Persistent Expression of Human Clotting Factor IX from Mouse Liver after Intravenous Injection of Adeno–Associated Virus Vectors", Proc. Natl. Acad. Sci. USA 94:1426–1431.

Vincent et al., 1997, "Analysis of Recombinant Adeno–Associated Virus Packaging and Requirments for rep and cap Gene Products", J. Virol. 71:1897–1905.

Pereira et al., 1996, "The Adeno–Associated Virus (AAV) Rep Protein Acts as both a Repressor and an Activator to Regulate AAV Transcription during a Productive Infection", J. Virol. 71:1079–1088.

Clark et al., 1995, "Cell Lines for the Production of Recombinant Adeno–Associated Virus", Human Gene Ther. 6:1329–1341.

Flotte and Carter, 1995, "Adeno–Associated Virus Vectors for Gene Therapy", Gene Ther. 2:357–362.

Flotte et al., 1995, "An Improved System for Packaging Recombinant Adeno–Associated Virus Vectors Capable of In Vivo Transduction", Gene Ther. 2:29–37.

Horer et al., 1995, "Mutational Analysis of Adeno–Associated Virus Rep Protein–Mediated Inhibition of Heterologous and Homologous Promoters", J. Virol. 69:5485–5496.

Giraud et al., 1994, "Site–Specific Integration by Adeno–Associated Virus Is Directed by a Cellular DNA Sequence", Proc. Natl. Acad. Sci USA 91:10039–10043.

Hermonat, 1994, "Down–Regulation of the Human c–fos and c–myc Proto–Oncogene Promoters by Adeno–Associated Virus Rep78", Cancer Lett. 81:129–136.

Yang et al., 1994, "Characterization of Cell Lines that Inducibly Express the Adeno–Associated Virus Rep Proteins", J. Virol. 68:4847–4856.

Muzyczka, 1992, "Use of Adeno–Associated Virus as a General Transduction Vector for Mammalian Cells", Curr. Top. Microbiol. Immunol. 158:97–129.

Antoni et al., 1991, "Adeno–Associated Virus Rep Protein Inhibits Human Immunodeficiency Virus Type 1 Production in Human Cells", J. Virol. 65:396–404.

Muzyczka, 1991, "In Vitro Replication of Adeno–Associated Virus DNA", Virol. 2:281–290.

McCarty et al., 1991, "Sequence Required for Coordinate Induction fo Adeno–Associated Virus p19 and p40 Promoters by Rep Protein", J. Virol. 65:2936–2945.

Samulski et al., 1991, "Targeted Integration of Adeno–Associated Virus (AAV) into Human Chromosome 19", EMBO J. 10:3941–3950.

Heilbronn et al., 1990, "The Adeno–Associated Virus rep Gene Suppresses Herpes Simplex Virus–Induced DNA Amplification", J. Virol. 64:3012–3018.

Chejanovsky and Carter, 1989, "Mutagenesis of an AUG Codon in the Adeno–Associated Virus rep Gene: Effects on Viral DNA Replication", Virol. 173:120–128.

Samulski et al., 1989, "Helper–Free Stocks of Recombinant Adeno–Associated Viruses: Normal Integration Does Not Require Viral Gene Expression", J. Virol. 63:3822–3828.

Lebkowski et al., 1988, "Adeno–Associated Virus: A Vector System for Efficient Introduction and Integration of DNA into a Variety of Mammalian Cell Types", Mol. Cell. Biol. 8:3988–3996.

Labow et al., 1987, "Adeno–Associated Virus Gene Expression Inhibits Cellular Transformation by Heterologous Genes", Mol. Cell. Biol. 7:1320–1325.

Guarino and Summers, 1986, "Interspersed Homologous DNA of Autographa californica Nuclear Polyhedrosis Virus Enhances Delayed–Early Gene Expression", J. Virol. 60:215–223.

Kozak, 1986, "Point Mutations Define a Sequence Flanking the AUG Initiator Codon that Modulates Translation by Eukaryotic Ribosomes", Cell 44:283–292.

Tratschin et al., 1986, "Negative and Positive in trans of Gene Expression from Adeno–Associated Virus Vectors on Mammalian Cells by a Viral rep Gene Product", Mol. Cell. Biol. 6:2884–2894.

*Primary Examiner*—David Guzo
*Attorney, Agent, or Firm*—Pennie & Edmonds LLP

[57] ABSTRACT

The present invention relates to methods and compositions for increasing the production of high titre stocks of recombinant AAV (rAAV) through regulation of expression of the AAV REP and CAP proteins. The methods and compositions of the invention are based on the observation that the low level expression of the AAV REP 78/68 protein increases the production of AAV viral capsid protein and efficiency of packaging resulting in production of higher titre recombinant viral stocks. The invention encompasses recombinant AAV vectors that direct the expression of AAV REP and CAP proteins and the use of such vectors for the production of novel stable cell lines capable of generating high titre rAAV vectors. The invention provides methods for regulating the expression of the AAV REP 78/68, REP 40/52 and CAP gene at the transcriptional and post-translational level. The methods and compositions of the invention can be used to produce high titre stocks of rAAV which can be used in gene therapy for the purpose of transferring genetic information into appropriate host cells for the management and correction of human diseases including inherited and acquired disorders.

12 Claims, 8 Drawing Sheets

METHOD FOR INCREASING THE EFFICIENCY OF RECOMBINANT AAV PRODUCTION

1. INTRODUCTION

The present invention relates to methods and compositions for increasing the production of high titre stocks of recombinant AAV (rAAV) through regulation of expression of the AAV REP and CAP proteins. The methods and compositions of the invention are based on the observation that the low level expression of the AAV REP 78/68 protein increases the production of AAV viral capsid protein and efficiency of packaging resulting in production of higher titre recombinant viral stocks. The invention encompasses recombinant AAV vectors that direct the expression of AAV REP and CAP proteins and the use of such vectors for the production of novel stable cell lines capable of generating high titre rAAV vectors. The invention provides methods for regulating the expression of the AAV REP 78/68, REP 40/52 and CAP gene at the transcriptional and post-translational level. The methods and compositions of the invention can be used to produce high titre stocks of rAAV which can be used in gene therapy for the purpose of transferring genetic information into appropriate host cells for the management and correction of human diseases including inherited and acquired disorders.

2. BACKGROUND OF THE INVENTION

2.1. Gene Therapy

Gene therapy is generally understood to refer to techniques designed to deliver functionally active therapeutic genes into targeted cells. Such therapeutic genes may encode proteins that complement genetic deficiencies, cytokines, cell surface membrane proteins or any protein that functions to regulate cell growth and/or differentiation. Such proteins may function intracellularly, for example, by regulating a signalling pathway or transcriptional pathway. Alternatively, the proteins may be secreted by the cell and exert their effect extracellularly.

Initial efforts toward somatic gene therapy have relied on indirect means of introducing genes into tissues, e.g., target cells are removed from the body, transfected or infected with vectors carrying recombinant genes, and reimplanted into the body. These types of techniques are generally referred to as in vitro treatment protocols.

In contrast, direct in vivo gene transfer has recently been achieved with formulations of DNA trapped in liposomes (Ledley et al., 1987); or in proteoliposomes that contain viral envelope receptor proteins (Nicolau et al, 1983); calcium phosphate-coprecipitated DNA (Benvensisty & Reshef, 1986); and DNA coupled to a polylysine-glycoprotein carrier compounds (Wu & Wu, 1988).

In addition, recombinant replication-defective viral vectors have been used to infect cells both in vitro and in vivo. Perhaps the most widely studied viral vectors for use in gene therapy have been the retroviral vectors. The major disadvantages associated with the use of retroviral vectors include the inability of many viral vectors to infect non-dividing cells, problems associated with insertional mutagenesis and potential helper virus production. Recently, attention has turned to the use of other types of recombinant viral vectors such as adenovirus and adeno-associated virus based vectors, that may be used to deliver genes of interest to cells.

In particular, recombinant adeno-associated virus has many features of interest in the field of gene therapy. The vectors are based on a defective, nonpathogenic human parvovirus that can infect both dividing and non-dividing cells without a marked tropism. In addition, the viral genome can stably integrate within the host genome, facilitating long term gene transfer.

2.2. AAV Viral Vectors

The AAV genome is composed of a linear single stranded DNA molecule of 4680 nucleotides which contains major open reading frames coding for the Rep (replication) and Cap (capsid) proteins. Flanking the AAV coding regions are two 145 nucleotide inverted terminal (ITR) repeat sequences that contain palindromic sequences that can fold over to form hairpin structures that function as primers during initiation of DNA replication. In addition, the ITR sequences are needed for viral integration, rescue from the host genome and encapsidation of viral nucleic acid into mature virions (Muzyczka, N., 1992, Current Topics in Microbiology & Immunology. 158, 97–129).

AAV can assume two pathways upon infection into the host cell depending on whether helper virus is present. In the presence of helper virus, AAV will enter the lytic cycle whereby the viral genome is transcribed, replicated, and encapsidated into newly formed viral particles. In the absence of helper virus function, the AAV genome will integrate as a provirus into a specific region of the host cell genome through recombination between the AAV termini and host cell sequences (Cheung, A. et al., 1980, J. Virol. 33:739–748; Berns, K.I. et al., 1982, in virus Persistence, eds. Mahey, B.W.J., et al. (Cambridge Univ. Press, Cambridge), pp. 249–265).

The use of AAV as a vehicle for the transfer of genetic information has been facilitated by the discovery that when a plasmid containing an intact AAV genome is transfected into a host cell the recombinant AAV vector will integrate into the host cell genome and remain as a provirus until the host cell subsequently becomes infected with a helper virus. Upon infection of the host cell with helper virus, the AAV is rescued out from the plasmid vector and enters the lytic cycle leading to production of mature virions.

The production of rAAV particles, utilizes a vector containing a transgene flanked by the inverted terminal repeats (ITR), which are the sole AAV cis sequences required for DNA replication, packaging and integration. To produce rAAV particles, the AAV (Rep) and capsid (Cap) gene products are normally provided in trans from a different template, usually a helper plasmid.

The three viral coat proteins, VP1, VP2, and VP3 which are required for virion expression are derived from mRNA initiated at the p40 promoter, while the four overlapping non-structural Rep proteins are essential for AAV DNA replication. Rep78 and 68 are expressed from unspliced and spliced transcripts initiating at the p5 promoter, while Rep52 and Rep40 are similarly produced from transcripts initiating at the p19 promoter. Although Rep52/40 have been implicated in AAV single stranded DNA formation (Chejanovsky et al., 1989, Virology 173:120–128) and gene regulation, Rep78/68 appear to display all enzyme functions essential for AAV DNA replication, (ITR binding, DNA helicase, and DNA site-specific nicking activity), (Muzyczka, N., 1991, Seminars in Virology 2:281–290). In addition to these functions, Rep78/68 both positively and negatively regulate AAV promoters (Labow et al., 1986, Journal of Virology 60:215–258; Pereira et al., 1997, J. Virol, In Press; Tratschin et al., 1986, Mol. Cell Biol. 6:2884–2894) and repress numerous heterologous promoters (Antoni et al., 1991, Journal of Virology 65:396–404; Heilbronn et al., 1990, Journal of Virology 64:3012–3018; Hermonat, P.L., 1994, Cancer Letters 81:129–36; Horer, et al., 1995, Journal of Virology 69:5485–5496; Labow et al., 1987, Molecular & Cellular Biology 7:1320–1325).

Rep gene expression appears to be critical for all steps of the AAV life cycle, including a latent state which occurs in the absence of a helper virus (Berns, K.I., 1990, Virology, 2ed, vol. 2; Berns, K.I., 1996, B.N. Fields et al. ed.; Samulski et al., 1989, Journal of Virology 63:3822–3828). Recently, Rep78/68 have also been associated with AAV integration into the host genome (Giraud et al., 1994, Proceedings of the National Academy of Sciences of the United States of America; Kotin et al., 1990, Proceedings of the National Academy of Sciences of the United States of America 87:221–2215; Samulski et al., 1991, EMBO Journal 10:3941–3950; Weitzmann et al., 1994, Proceedings of the National Academy of Sciences of the United States of America 91:5808–5812). Repression of viral gene expression by rep and host YY1 protein appears to be required for establishment and maintenance of the latent state (Labow et al., 1986, Journal of Virology 60:251–258; Laughlin et al., 1982, Journal of Virology 41:868–876; Periera et al., 1997, J. Virol In Press; Shi et al., 1991, Cell 67:377–388). Such repression may be necessary to avoid the demonstrated cytostatic effect on the host cell by Rep gene products (Yang et al., 1994, Journal of Virology 68:4847–4856). During a lytic infection, the AAV promoters, particularly p5, are transactivated by the adenovirus E1A proteins and YY1 (Lewis, et al., 1995, J. Virol. 69:1628–1636; Shi et al., 1991, Cell. 67:377–388). The p5 products then positively regulate the p19 and p40 promoters, resulting in abundant production of Rep 52/40 and viral capsid proteins (Pereira et al., 1997, J. Virol. 71:1079–1088). Early efforts to by-pass AAV rep gene regulation by substituting the p5 promoter with the SV40 early promoter have failed (Labow et al., 1988, Journal of Virology 62:1705–1712). Instead of constitutive Rep78/68 expression, the heterologous promoter unexpectedly behaved in the same manner as the endogenous p5 promoter; repressed in the absence and activated in the presence of Ad (Labow et al., 1988, Journal of Virology 62:1750–1712). While these studies were the first to suggest rep repression as a mechanism for regulating heterologous promoters, these findings also implied that AAV p5 products may be a rate-limiting factor in AAV production (Labow et al., 1988, Journal of Virology 62:1705–1712). Further efforts in this area have suggested that overexpression of Rep78/68 may increase rAAV vector yields (Flotte et al., 1995, Gene Therapy 2:29:37).

An essential feature for use of rAAV as an efficient delivery system is the ability to produce recombinant stocks of virus. Although rAAV titres can approach wild type (wt) levels after multiple rounds of purification and concentration, the overall total yield is still substantially lower than that of wild type AAV. Therefore, methods that increase the ability to produce high titre rAAV viral stocks will facilitate the use of rAAV delivery systems in gene therapy.

3. SUMMARY OF THE INVENTION

The present invention provides novel recombinant AAV vectors and rAAV packaging cell lines that may be used in the production of high titre stocks of recombinant AAV. The invention is based on the discovery that decreased expression of AAV REP 78/68 proteins results in increased synthesis of viral capsid proteins and replication of viral DNA resulting in production of high titre recombinant viral stocks. Such recombinant AAV stocks may be used in gene therapy for the purpose of transferring genetic information into appropriate host cells for the management and correction of human disease including inherited and acquired disorders such as cancer and AIDS.

The invention encompasses methods for production of high titre stocks of recombinant AAV by regulating REP 78/68 expression levels and/or the activity of the AAV REP 78/68 proteins in a host cell. The invention encompasses compositions such as recombinant helper plasmids that are genetically engineered to express low levels of biologically functional viral REP 78/68 proteins. In such helper plasmids the expression of REP 78/68 proteins may be regulated at the transcriptional, translational and/or post-translational level. The invention further relates to recombinant helper plasmids that are genetically engineered to express high levels of the AAV REP 40/52 and CAP genes. In addition, host cells can be genetically engineered to contain the separate plasmids expressing each of the AAV REP and CAP genes.

4. BRIEF DESCRIPTION OF THE DRAWINGS

FIG. 1. Map of the AAV Genome.

Figure 2:
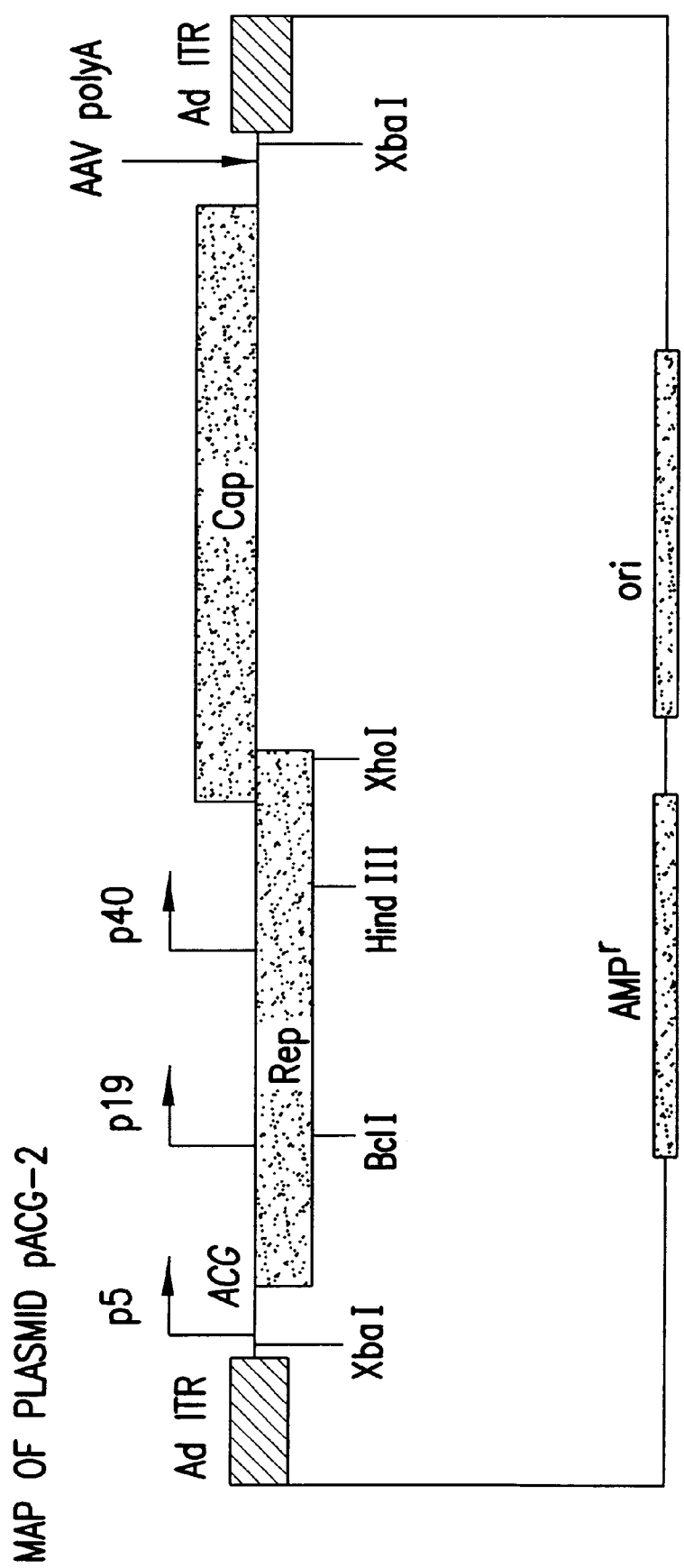

FIG. 2. Map of pACG-2. Plasmid ACG-2 contains the endogenous p5 promoter and has an ATC to ACG mutation at the translation initiation codon of REP 78/68.

Figure 3:
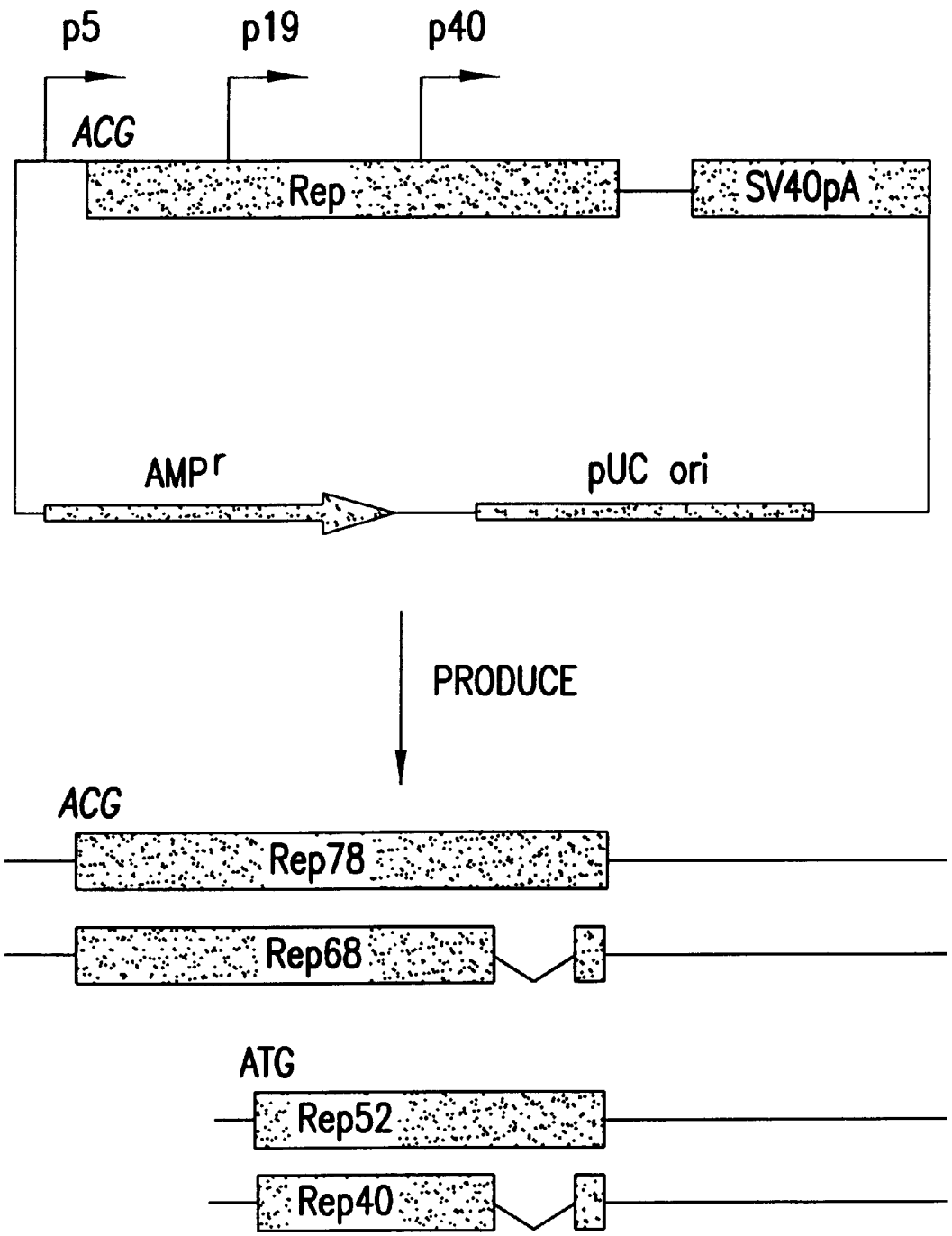

FIG. 3. Map of Plasmid pACG-REP. Plasmid PACG-REP contains the AAV REP gene under the control of the p5 promoter and has anATC to ACG mutation at the translation intiation codon.

Figure 4:
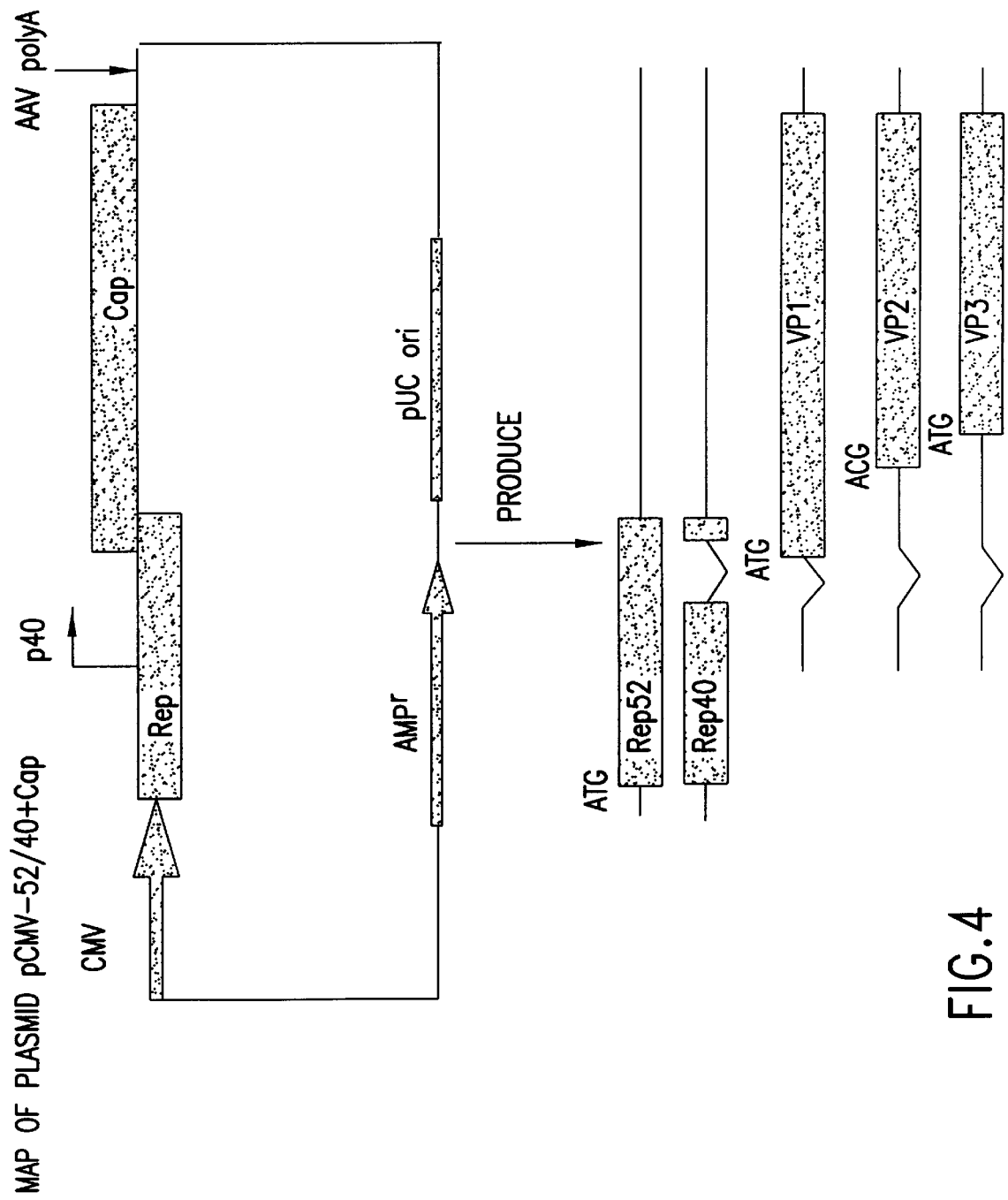

FIG. 4. Map of Plasmid pCMV-52/40+Cap. Plasmid pCMV-52/40 CAP contains the AAV REP 40/52 and CAP under the control of the CMV promoter.

Figure 5:
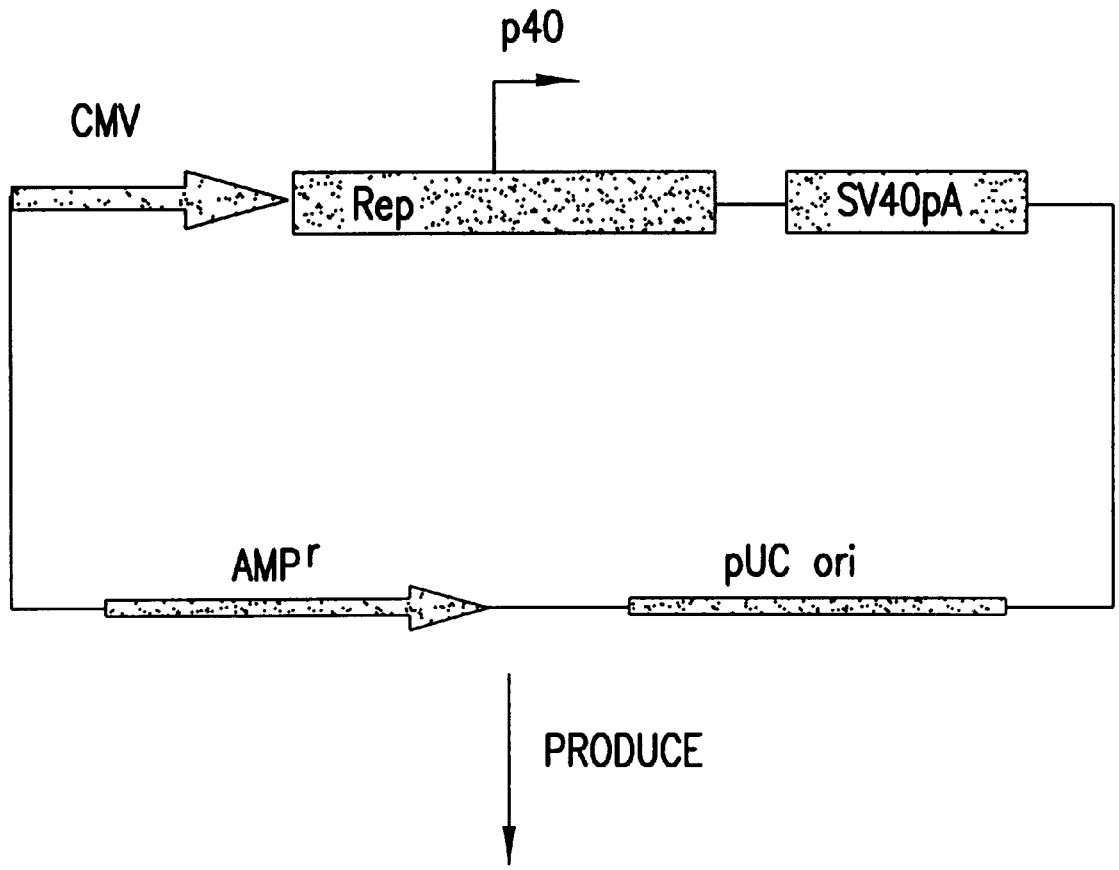

FIG. 5. Map of Plasmid pCMV-52/40. Plasmid pCMV-52/40 contains the AAV REP 40/52 under the control of the CMV promoter.

Figure 6:
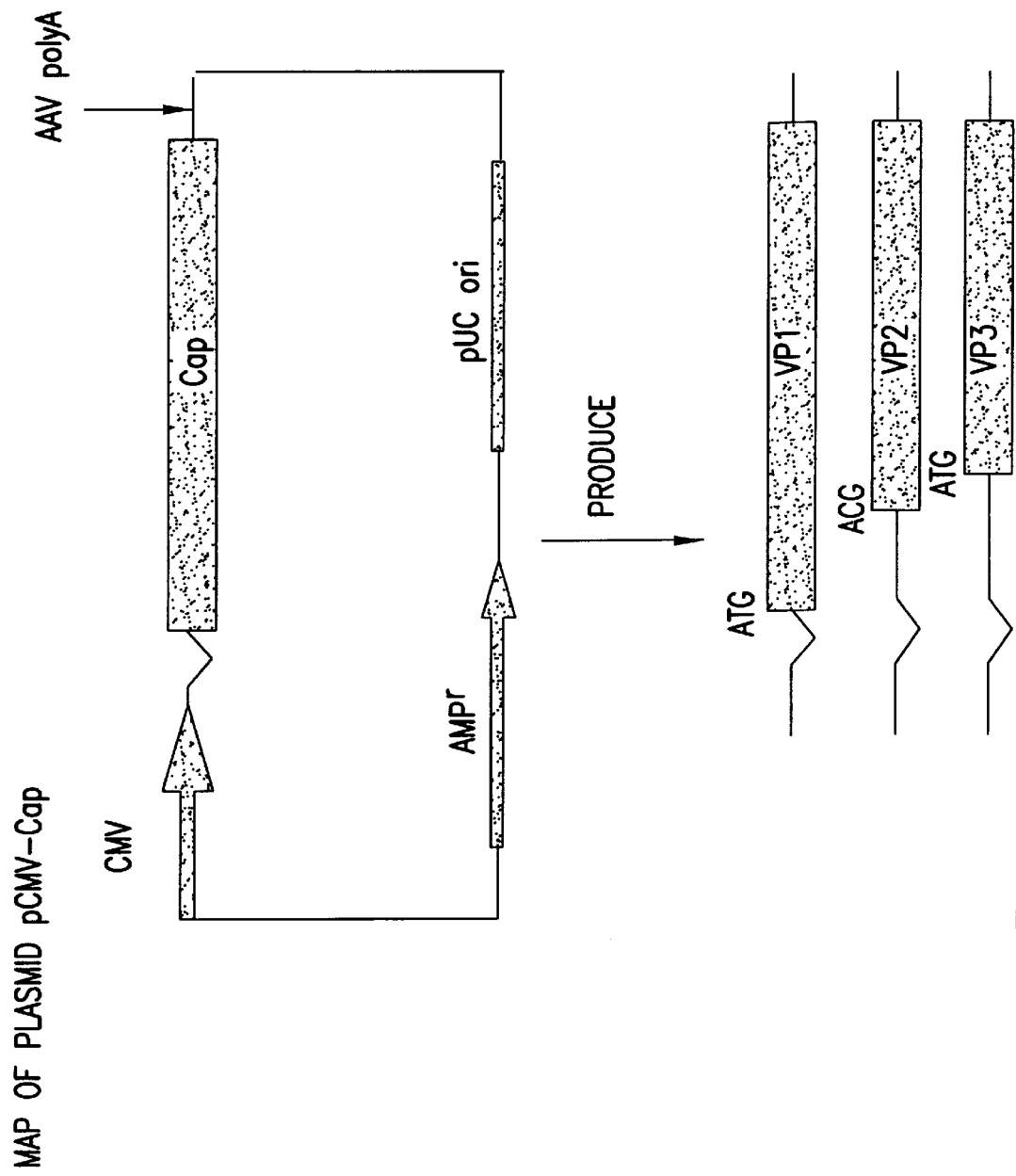

FIG. 6. Map of Plasmid pCMV-Cap. Plasmid pCMV-CAP contains the AAV CAP gene under the control of the CMV promoter.

Figure 7:
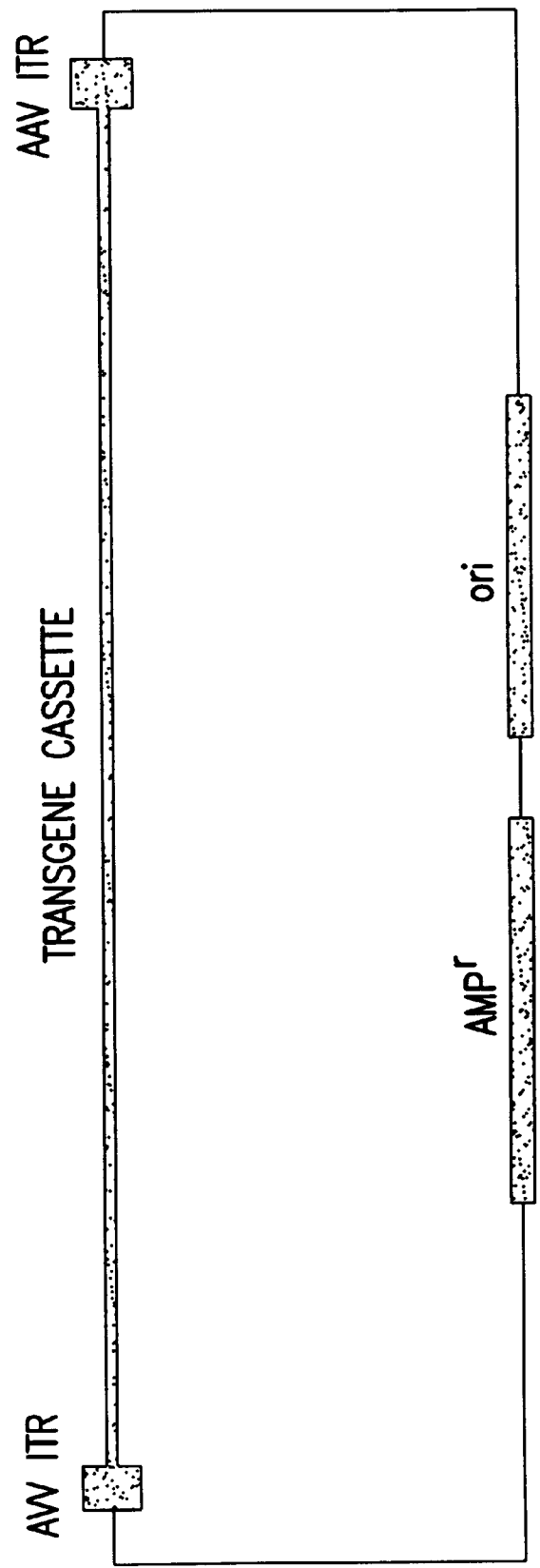

FIG. 7. Map of recombinant AAV vector plasmid. Plasmid contains a transgene cassette insert between the two AAV ITR sequences.

Figure 8:
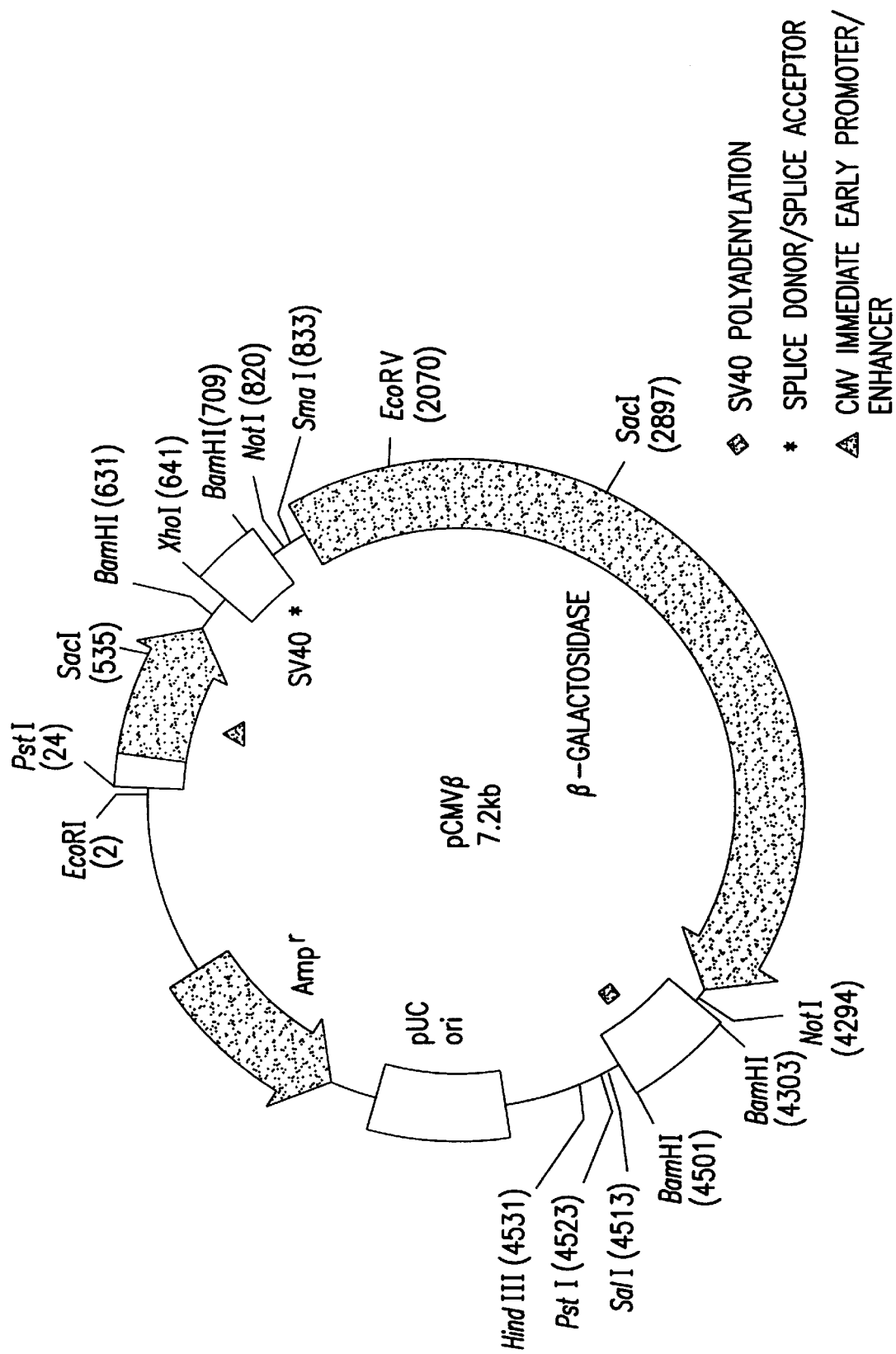

FIG. 8. Map of pCMVB.

5. DETAILED DESCRIPTION OF THE INVENTION

The present invention relates to methods for increasing the production of high titre stocks of recombinant AAV (rAAV) through regulation of expression of the AAV REP 78/68, REP 40/52 and CAP proteins. To generate recombinant viral stocks, a recombinant vector containing a gene of interest and the cis-required AAV terminal repeat sequences is transfected into a host cell that is capable of providing helper virus function, and supplying in trans AAV REP and CAP proteins. The methods of the invention are based on the observation that low level in trans expression of the AAV REP 78/68 proteins increases the production of AAV viral capsid protein and efficiency of packaging of rAAV vectors resulting in production of higher titre recombinant viral stocks.

In particular, the invention described in the subsections below encompasses methods for regulating the level of REP 78/68, REP 40/52 and CAP protein expression. The invention relates to recombinant helper plasmids that are genetically engineered to express low levels of AAV viral REP 78/68 protein and high levels of REP 40/52 and CAP proteins. For example, expression of the various AAV proteins may be regulated at the level of transcription through the use of physically separated and distinct plasmids containing tightly controlled promoter systems. For example, the native AAV p19 and p40 promoters can be replaced with strong heterologous promoters such as the cytomeglavirus immediate early (CMV IE) promoter. The use of strong heterologous promoters alleviates the modulating efforts of the AAV REP 78/68 proteins on the p19 and p40 promoters.

Alternatively, the ratios of the different plasmid constructs may be manipulated in such a way that more copies of the REP 40/52 and CAP genes under the transcriptional control of their native promoters (p19 and p40), versus the REP 78/68 genes under the transcriptional control of its native AAV promoter (p5), are introduced into the host cell line.

In yet another embodiment, the ratios of the plasmid constructs may be manipulated in such a way that more REP 40/52 and CAP genes plasmid constructs under heterologous promoters (such as CMV IE) versus the REP 78/68 under its native AAV promoter (p5) will be introduced to make the cell line. In such instances, the expression of REP 78/68 proteins can be from the native promoter (p5) and translational start codon (ATG), from a heterologous promoter, from a non-native translational start codon (ACG), or any combination thereof.

The AAV expression vectors can be used transiently for the production of recombinant AAV stocks. Alternatively, the recombinant plasmids may be used to generate stable packaging cell lines. To create a stable producer cell line, the recombinant vectors expressing the AAV genes may be cotransfected into host cells with a plasmid expressing the neomycin phosphotransferase gene (neor) by transfection methods well known to those skilled in the art, followed by selection for G418 resistance.

In addition to producing high titres of recombinant virus stocks, the production of cell lines with three different plasmid vectors directing the expression of the AAV REP and CAP genes will reduce the probability of producing contaminating wild type AAV. To generate an infectious wild type AAV genome would require multiple recombination events in order to generate an infectious wild type genome.

5.1. Recombinant Expression Of AAV REP Protein

The present invention encompasses recombinant helper plasmids that are genetically engineered to provide in trans low level expression of viral REP and CAP proteins. In accordance with the invention the open reading frame which encodes the AAV REP 78/68, REP 40/52 and CAP (VP1, VP2 and VP3 genes) proteins may be engineered into expression vectors for highly regulated expression of the REP proteins. In order to express AAV REP and CAP proteins, the nucleotide sequences coding for the REP and CAP proteins, or functional equivalents, is inserted into an appropriate expression vector, i.e., a vector which contains the necessary elements for the highly regulated transcription and translation of the inserted REP and CAP coding sequences.

Methods which are well known to those skilled in the art can be used to construct expression vectors containing the AAV REP and CAP protein coding sequences operatively associated with appropriate transcriptional/translational control signals for highly regulated expression of REP and CAP. These methods include in vitro recombinant DNA techniques, synthetic techniques, and in vivo recombinatior/ genetic recombination. See, for example, the techniques and vectors described in Maniatis, et al., 1989, Molecular Cloning, A Laboratory Manual, Cold Spring Harbor Laboratory, N.Y. and Ausubel et al., 1989, Current Protocolsin Molecular Biology, Greene Publishing Associates & Wiley Interscience, N.Y.

The sequences of the AAV REP and CAP genes are reported in Srivastava, A., et al., 1983, J. Virol. 45:555–564; Muzyczka, N., 1992, Curr. Top. Micro Immunol. 158:97–129, and Ruffing, M., et al., 1992, J. Virol. 66:6922–6930, 1992. Sources for the AAV REP and CAP genes may include the mammalian virus serotypes AAV-1, AAV-2, AAV-3, AAV-4, and AAV-5, as well as bovine AAV and avian AAV. The invention contemplates, in addition to the REP and CAP DNA sequences disclosed therein, (1) any DNA sequence that encodes the same amino acid sequence for REP 78/68, REP 40/52 and CAP shown in Srivastava, A., et al., supra; Muzyczka, N., supra and Ruffing, M., et al. supra; (2) any DNA sequence that hybridizes to the complement of the coding sequences disclosed therein under highly stringent conditions, e.g., washing in 0.1×SSC/0.1% SDS at 68° C. (Ausubel F.M. et al., eds., 1989, Current Protocols in Molecular Biology, Vol. I, Green Publishing Associates, Inc., and John Wiley & sons, Inc., New York, at p. 2.10.3) and encodes a functionally equivalent gene product; and/or 3) any DNA sequence that hybridizes to the complement of the coding sequences disclosed therein under less stringent conditions, such as moderately stringent conditions, e.g., washing in 0.2×SSC/0.1% SDS at 42° C. (Ausubel et al., 1989, supra), yet which still encodes a functionally equivalent gene product.

Nucleic acids which encode derivatives (including fragments) and analogs of native AAV REP and CAP proteins can also be used in the present invention, as long as such derivatives and analogs retain the ability to provide the functions required for AAV DNA replication and encapsidation of DNA into viral particles. In particular, REP and CAP derivatives can be made by altering REP or CAP sequences by substitutions, additions, or deletions that provide for functionally active molecules that may have a altered phenotype. Furthermore, due to the degeneracy of nucleotide coding sequences, other DNA sequences which encode substantially the same or a functionally equivalent AAV REP and CAP amino acid sequence may be used in the practice of the methods of the invention. The gene product may contain deletions, additions or substitutions of amino acid residues within the sequence which result in silent changes thus producing a bioactive product. Such amino acid substitutions may be made on the basis of similarity in polarity, charge, solubility, hydrophobicity, hydrophilicity and/or the ampipathic nature of the residues involved. For example, negatively charged amino acids include aspartic acid and glutamic acid; positively charged amino acids include lysine and arginine; amino acids with uncharged polar head groups or nonpolar head groups having similar hydrophilicity values include the following: leucine, isoleucine, valine, glycine, alanine, asparagine, glutamine, serine, threonine, phenylalanine, tyrosine.

A variety of host-expression vector systems may be utilized to express the AAV REP and CAP proteins. The expression systems that may be used for purposes of the invention include but are not limited to mammalian cell systems (e.g., COS, CHO, BHK, 293, 3T3, A549) harboring recombinant expression constructs containing regulatory elements derived from the genome of mammalian cells (e.g., metallothionein promoter) or from mammalian viruses (e.g., the adenovirus late promoter; the vaccinia virus 7.5 K promoter). Regulatory elements include, but are not limited to, inducible and non-inducible promoters, enhancers, operators and other elements known to those skilled in the art that drive and regulate expression. Promoters to express the REP and CAP proteins within a cell line may be drawn from those that are highly regulated within the host cell. They may include, but are not limited to, the CMV promotor, the SV40 promoter, the herpes TK promoter, and others well known in recombinant DNA technology. Inducible gene regulation may be achieved using simple inducible promoter systems, including but. not limited to, the metallothionine promoter (MT) and heat. shock promoter, or by using the mouse mammary tumor virus promoter (MMTV) which is responsive to glucocorticoid stimulation. Alternatively, a more flexible though more complex inducible regulation system can be achieved through a "binary" gene approach. These binary regulation systems utilize a transactivator gene product to control expression of a second gene of interest. In addition, repressor based binary systems may be used to regulate gene expression (Brown et al., 1987, Cell 48:555–566; Figge et al., 1988, Cell 49:603–612). For example, the tetR system utilizes the bacterial repressor tetR and insertion of tetR operator sequences in the promoter region of a gene of interest. Induction of gene expression in such a system involves the application of an inducer molecule that binds to and inactivates the repressor molecule resulting in activation of gene expression.

The REP and CAP coding region may be linked to any number of promoters in an expression vector that can be activated in the chosen cell line. Additionally, this cassette (REP or CAP genes and promoter) is carried by a vector that contains a selectable marker so that cells receiving the vector may be identified. Selectable markers and their attendant selection agents can be drawn from the group including but not limited to aminoglycoside phosphotransferase/G418, hygromycin-B phosphotransferase/hygromycin-B, and amplifiable selection markers such as dihydrofolate reductase/methotrexate and others known to skilled practitioners.

Other embodiments of the present invention include the use of procaryotic, insect, plant, and yeast expression systems to express the AAV REP and CAP proteins. In order to express REP and CAP proteins the nucleotide sequence coding for the REP and CAP proteins, or a functional equivalent as described in Section 5.1, supra, are inserted into an appropriate expression vector, i.e., a vector which contains the necessary elements for the transcription and translation of the inserted coding sequences. Methods which are well known to those skilled in the art can be used to construct expression vectors containing the REP and CAP protein coding sequences operatively associated with appropriate transcriptional/translational control signals. These methods include in vitro recombinant DNA techniques, synthetic techniques, and in vivo recombination/genetic recombination. See, for example, the techniques and vectors described in Maniatis, et al., 1989, Molecular Cloning, A Laboratory Manual, Cold Spring Harbor Laboratory, N.Y. and Ausubel et al., 1989, Current Protocolsin Molecular Biology, Greene Publishing Associates & Wiley Interscience, N.Y.

Specific initiation signals are also required for sufficient translation of inserted protein coding sequences. These signals include the ATG initiation codon and adjacent sequences. These exogenous translational control signals and initiation sequences can be of a variety of origins, both natural and synthetic. For example, *E. coli* expression vectors will contain translational control sequences, such as an appropriately positioned ribosome binding site and initiation ATG.

The expression of REP 78/68 proteins may be regulated at the transcriptional level through the use of tightly controlled promoter systems that result in either low level, or inducible, expression of the REP 78/68 gene. Such promoters can be genetically engineered into recombinant helper plasmids that are designed to express low levels of REP 78/68 protein. Further, triple helix molecules can be utilized to reduce the level of REP 78/68 gene expression. Such triple helix molecules can be designed to hybridize to the promoter region of the REP 78/68 gene and thereby inhibit REP gene transcription.

Still further, the invention encompasses recombinant helper plasmids that are genetically engineered to regulate the translation of REP 78/68 mRNA. For example, the coding region of the REP genes may be genetically engineered to replace the initiator MET codon with a less efficiently translated initiator codon. For example, a recombinant plasmid may be constructed to contain an ATG to ACG mutation in the start codon of REP 78/68.

The genes encoding the viral REP 78/68 proteins can also be genetically engineered to contain specific 5' nucleotide sequences to which translation repressor proteins bind (Melefors, 1993, Bioessays 15:85–90). The binding of such repressor proteins to the 5' end of the REP 78/68 MRNA molecules will result in inhibition of REP 78/68 mRNA translation. Using such a system, the level of REP protein maybe controlled by regulating the level or activity of the translational repressor protein. Such sequences include, but are not limited to, sequences such as the iron-response element.

Alternatively, the level of REP 78/68 mRNA translation may be controlled by altering the stability of REP mRNA. For example, the half life of the REP 78/68 mRNAs may be significantly decreased by genetically engineering nucleotide sequences rich in A and U nucleotides in the 3' untranslated region (UTR). Additionally, REP 78/68 mRNAs containing recognition sites in their 3' UTR for specific endonucleases may be generated using recombinant DNA techniques.

In addition, the translation of REP 78/68 mRNA may be controlled through cloning of specific mRNA recoding signals into the REP genes. Such recoding signals in the REP 78/68 mRNA molecule will cause the growing REP 78/68 polypeptide chains to occasionally slip backward by one nucleotide on the ribosome causing the mRNA to be read in the incorrect reading frame and leading to production of a truncated REP proteins. In an embodiment of the invention, a recoding signal sequence which consists of the nucleotides UUUUUUA, may be included in AAV REP encoding recombinant helper plasmids to produce the desired low levels of AAC REP protein.

The level of REP 78/68 protein expressed in a host cell may further be reduced through the use of antisense and ribozyme molecules. Antisense approaches involve the design of oligonucleotides that bind to the complementary REP RNA and suppress translation of REP RNA. Ribozymes molecules may be designed that include one or more sequences complementary to REP RNA and which function to specifically and efficiently catalyses endonucleolytic cleavage of REP RNA sequences.

Finally, the activity of the REP 78/68 proteins may also be regulated at the post-translational level. For example, mutant forms of the REP 78/68 proteins may be generated that have decreased activity and/or decreased protein stability. The activity of the REP 78/68 proteins may be regulated through the use of temperature sensitive REP mutants. Alternatively, REP proteins which are less stable, i.e., REP proteins that possess a shorter half-life or REP proteins that are more susceptible to proteolytic cleavage, may be utilized as a means for decreasing the activity of the REP proteins.

5.2. Cell Lines Engineered to Express The AAV REP and CAP Protein

Cell lines may be engineered that will natively express low levels of the AAV REP 78/68 proteins and high levels of the REP 40/52 and CAP proteins. To engineer an AAV REP and CAP producing cell line, cells can be transfected with recombinant helper plasmids vector into which the AAV REP and CAP open reading frame has been inserted. Standard recombinant DNA techniques may be used to construct the recombinant vectors using the methods described above in Section 5.1. (Ausubel, F. et al., eds., Current Protocols in Molecular Biology, Wiley & Sons, New York, 1994). Transfection may be accomplished with any of the standard techniques in the art. Alternatively, a cell line can be established with the use of viral vectors that are capable of integrating DNA into the host cell genome. Examples of these vectors include those derived from retroviruses or AAV.

Cell lines which may be chosen for integration include but are not limited to HeLa, COS, NIH 3T3, A549 and others well known to those skilled in the art. The REP and CAP coding regions may be linked to any number of heterologous promoters that can be activated in the chosen cell line. Additionally, this insertion cassette (REP and CAP genes and promoter) may be linked to a gene coding for a selectable marker, in which case the integration of the REP and/or CAP coding region with the linked marker will confer the particular phenotype afforded by the marker to a stably transfected cell. Thus, the cells that have successfully integrated the REP and/or CAP genes will be selectable. Alternatively, the selectable marker may be transfected on a separate plasmid.

Promoters to express the AAV REP and CAP proteins within a cell line may be drawn from those that are functionally active within the host cell. Such promoters, which are well known in the art, will include those promoters that are highly regulated within the host cell resulting in low level expression of the viral REP 78/68 proteins or in high level expression of the REP 40/52 and CAP protein. Inducible promoters may be also be used in the practice of the invention, including but not limited to, the metallothionine promoter (MT), the mouse mammary tumor virus promoter (MMTV), and others known to those skilled in the art.

Selectable markers and their attendant selection agents can be drawn from the group including but not limited to aminoglycoside phosphotransferase/G418, hygromycin-B phosphotransferase/hygromycin-B, and amplifiable selection markers such as dihydrofolate reductase/methotrexate and others known to skilled practitioners.

Detection of the expression of the REP and CAP genes can be performed by standard techniques including Northern analysis, immunoblotting, and immunoprecipitation. Such techniques may be utilized to identify cells that express low levels of REP protein.

5.3. Production of Recombinant Virus Stocks

The present invention relates to methods for efficient production of high titre stocks of rAAV through regulation of expression of the AAV REP and CAP proteins. The methods of the invention comprised culturing a eukaryotic cell containing helper virus, recombinant DNA encoding AAV CAP and REP protein, and a recombinant nucleic acid containing a DNA sequence of interest and the required cis-acting AAV terminal repeat structures.

A primary goal of the present invention is to provide methods for expressing in trans low levels of REP 78/68 protein and high level expression of REP 40/52 and CAP. The methods of the invention are based on the observation that reduced expression or activity of the REP 78/68 protein results in production of high titre stocks of rAAV.

To generate recombinant viral stocks, the recombinant nucleic acid containing the DNA sequence of interest flanked by AAV ITRs may be transfected, or infected, into a host cell line that is capable of providing helper virus function, and supplying in trans AAV REP and CAP proteins. The REP and CAP proteins are required for replication and encapsidation of the linear recombinant nucleic acid into mature viral particles.

The REP and CAP proteins may be supplied in trans by transfection of the host cell line with recombinant plasmids that are capable of coding for each of the proteins. DNA transfections maybe carried out using methods well known to those skilled in the art. These may include DNA transfection by lipofection, electroporation or calcium phosphate precipitation (Ausubel, et al., 1989, in Current Protocols for Molecular Biology, Green Publishing Associates, Inc. and John Wiley & Sons, Inc., New York). The plasmid is transfected into the host cell line with the intention of either transiently or stably expressing the REP and CAP proteins.

In addition to expressing the viral REP and CAP proteins, the host cell lines must be able to provide helper virus function. Both adenovirus and herpes simplex virus may serve as helper viruses for replication and encapsidation of DNA fragments containing the cis-required AAV terminal repeat sequences. Any host cell permissive for infection by either of these two viruses or any virus that acts as a helper virus for AAV, may be used in the practice of the invention. The multiplicity of infection (MOI) and the duration of the infection time will depend on the type of virus used and the cell line employed and such techniques are well known to those skilled in the art.

5.4. Uses of Recombinant AAV Viral Stocks

The rAAV viral stocks may be used in gene therapy for the purpose of transferring genetic information into appropriate host cells for the management and correction of human diseases including inherited and acquired disorders such as cancer and AIDS. The rAAV can be administered to a patient at therapeutically effective doses. A therapeutically effective dose refers to that amount of the compound sufficient to result in amelioration of symptoms of disease.

Toxicity and therapeutic efficacy of the rAAV can be determined by standard pharmaceutical procedures in cell cultures or experimental animals, e.g., for determining the $LDS_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Doses which exhibit large therapeutic indices are preferred. While doses that exhibit toxic side effects may be used, care should be taken to design a delivery system that targets rAAV to the site of treatment in order to minimize damage to untreated cells and reduce side effects.

The data obtained from cell culture assays and animal studies can be used in formulating a range of dosage for use in humans. The dosage of such rAAV lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (ie., the concentration of the test compound which achieves a half-maximal infection or a half-maximal inhibition) as determined in cell culture. Such information can be used to more accurately determine useful doses in humans. Levels in plasma may be measured, for example, by high performance liquid chromatography.

Pharmaceutical compositions comprising the rAAV for use in accordance with the present invention, may be formulated in conventional manner using one or more physiologically acceptable carriers or excipients. For example, the rAAV may be suspended in a carrier such as PBS (phosphate buffered saline).

The rAAV and their physiologically acceptable salts and solvates may be formulated for administration by inhalation or insufflation (either through the mouth or the nose) or for oral, buccal, parenteral or rectal administration.

For administration by inhalation, the rAAV for use according to the present invention are conveniently delivered in the form of an aerosol spray presentation from pressurized packs or a nebulizer, with the use of a suitable propellant, e.g. dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of a therapeutic compound and a suitable powder base such as lactose or starch.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g. magnesium stearate, talc or silica); disintegrants (e.g. potato starch or sodium starch glycolate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound. For buccal administration the compositions may take the form of tablets or lozenges formulated in conventional manner.

The rAAV may be formulated for parenteral administration by injection e.g. by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder lyophilized form for constitution with a suitable vehicle, e.g., sterile pyrogen-free water, before use.

In addition to the formulations described previously, the rAAV may also be formulated as a depot preparation. Such long acting formulations may be administered by implantation (for example, subcutaneously or intramuscularly) or by intramuscular injection. Thus, for example, the therapeutic compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may for example, comprise metal or plastic foil, such as a blister pack. The pack or dispenser device may be accompanied by instructions for administration.

6. EXAMPLE: RECOMBINANT VIRAL VECTOR EXPRESSION OF AAV REP AND CAP GENES

The following subsection below describes the generation of recombinant AAV vectors engineered to express low levels of AAV REP 78/68 protein and high levels of AAV REP 40/52 and CAP proteins.

6.1. AAV Helper Plasmids Construction

To construct the plasmid pACG-Rep (FIG. 3), the plasmid pACG-2 (FIG. 2) is digested with restriction enzymes XbaI and XhoI and the Rep gene fragment (nucleotides 115 to 2163) is isolated. An oligonucleotide adaptor is ligated to the XhoI end of the fragment to replace the missing nucleotides in the rep gene (5'TCGAGGACACTCTCTCTGA3' (SEQ ID No: 1) annealed to 5'TCAGAGAGAGTGTCC3'(SEQ ID No: 2). The Rep gene fragment is then inserted into EcoRI and NotI restriction enzyme digested plasmid pCMBβ (FIG. 8; Clontech, #6177-1) with the 3' end of the rep gene proximal to the SV40 polyadenylation site of plasmid pCMVβ.

To construct the plasmid pCMV-52/40+Cap (FIG. 4), the plasmid pACG-2 (FIG. 2) is digested with restriction enzymes BcII and XbaI and the Rep+Cap gene fragment (nucleotides 894 to 4420) is isolated. The Rep+Cap gene fragment is then inserted into BamHI restriction enzyme digested plasmid pCMVβ (FIG. 8). To construct the plasmid pCMV-52/40 (FIG. 5), the plasmid pACG-2 (FIG. 2) is digested with restriction enzymes BcII and XhoI and the Rep gene fragment (nucleotides 894 to 2163) is isolated. An oligonucleotide adaptor is ligated to the XhoI end of the fragment to replace the missing nucleotides in the rep gene (5'TCGAGGACACTCTCTCTGA3' (SEQ ID No: 3) annealed to 5'CAGAGAGAGAGTGTCC3' (SEQ ID No: 4). This Rep gene fragment is then inserted into XhoI and NotI restriction enzyme digested plasmid pCMβ (Clontech, #6177-1) with the 5' end of the rep gene proximal to the CMV promoter of plasmid pCMβ. To construct the plasmid pCMV-Cap (FIG. 6), the plasmid pACG-2 (FIG. 2) is digested with restriction enzymes HindIII and XbaI and the Cap gene fragment (nucleotides 1812 to 4420) is isolated.

The Cap gene fragment is then inserted into BamHI restriction enzyme digested plasmid PCMβ (Clontech, #6177-1) with the 5' end of the Cap gene proximal to the CMV promoter of plasmid pCMVβ.

The present invention is not to be limited in scope by the specific embodiments described which are intended as single illustrations of individual aspects of the invention, and functionally equivalent methods and components are within the scope of the invention. Indeed, various modifications of the invention, in addition to those shown and descried herein will become apparent to those skilled in the art from the foregoing descriptions and accompanying drawings. Such modifications are intended to fall within the scope of the appended claims.

What is claimed:

1. A method for producing a stock of recombinant adeno-associated virus comprising:

a) co-transfecting cells permissive for adeno-associated virus replication with
   i) a recombinant vector engineered to express decreased levels of adeno-associated REP 76/68 protein with respect to levels of expression observed when the host cells express adeno-associated REP 76/68 under regulatory control of its native promoter;
   ii) a recombinant vector engineered to express increased levels of adeno-associated REP 40/52 and CAP protein with respect to levels of expression observed when the host cells express adeno-associated REP 40/52 and CAP under regulatory control of their native promoters; and iii) a recombinant adeno-associated virus vector which contains a foreign DNA sequence and which can be incorporated into an infectious AAV virion; and b) collecting the virions produced.

2. The method of claim 1 wherein the level of REP 78/68 protein is reduced by regulating the transcription of the REP 78/68 gene.

3. The method of claim 1 wherein the level of REP 78/68 protein is reduced by regulating the translation of the REP 78/68 gene.

4. The method of claim 1 wherein the transcription of the REP 40/52 and CAP genes is under the control of a heterologous promoter.

5. The method of claim 4 wherein the heterologous promoter is the cytomeglovirus promoter.

6. A host cell for producing a stock of recombinant adeno-associated virus containing:

i) a recombinant DNA vector that expresses less than the levels of adeno-associated REP 78/68 protein observed when the host cells express adeno-associated REP 76/68 under regulatory control of its native promoter; and ii) a recombinant DNA vector expressing the adeno-associated REP 40/52 and CAP protein.

7. The host cell of claim 6 wherein the level of REP 78/68 protein is regulated at the transcriptional level.

8. The host cell of claim 6 wherein the level of REP 78/68 protein is regulated at the translational level.

9. The host cell of claim 6 wherein the transcription of the REP 40/52 and CAP genes is under the control of a non-adeno-associated virus promoter.

10. The host cell of claim 6 wherein the host cell is transiently transfected.

11. The host cell of claim 6 wherein the host cell is stably transfected.

12. The host cell of claim 8 wherein the transcription of the REP 40/52 and CAP genes is under the control of the cytomeglovirus promoter.

* * * * *

SEQUENCE LISTING

```
<160> NUMBER OF SEQ ID NOS: 4

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 1
tcgaggacac tctctctga                                                 19

<210> SEQ ID NO 2
<211> LENGTH: 15
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 2
tcagagagag tgtcc                                                     15

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 3
tcgaggacac tctctctga                                                 19

<210> SEQ ID NO 4
<211> LENGTH: 16
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 4
cagagagaga gtgtcc                                                    16
```